(12) United States Patent
Webster

(10) Patent No.: US 9,394,526 B2
(45) Date of Patent: Jul. 19, 2016

(54) FROG/TOAD CONDITIONALLY SILENCED VECTORS FOR HYPOXIA GENE THERAPY

(75) Inventor: Keith A. Webster, Key Biscayne, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 13/504,438

(22) PCT Filed: Nov. 1, 2010

(86) PCT No.: PCT/US2010/054929
§ 371 (c)(1),
(2), (4) Date: Jul. 18, 2012

(87) PCT Pub. No.: WO2011/053896
PCT Pub. Date: May 5, 2011

(65) Prior Publication Data
US 2013/0131152 A1 May 23, 2013

Related U.S. Application Data

(60) Provisional application No. 61/256,381, filed on Oct. 30, 2009.

(51) Int. Cl.
*A61K 48/00* (2006.01)
*C12N 7/00* (2006.01)
*C07K 14/515* (2006.01)
*C07K 14/52* (2006.01)
*C12N 15/85* (2006.01)
*C12N 15/86* (2006.01)
*A61K 31/7088* (2006.01)

(52) U.S. Cl.
CPC .............. *C12N 7/00* (2013.01); *A61K 31/7088* (2013.01); *C07K 14/515* (2013.01); *C07K 14/52* (2013.01); *C12N 15/85* (2013.01); *C12N 15/86* (2013.01); *A61K 48/00* (2013.01); *C12N 2750/14121* (2013.01); *C12N 2750/14132* (2013.01); *C12N 2750/14143* (2013.01); *C12N 2830/002* (2013.01); *C12N 2830/32* (2013.01)

(58) Field of Classification Search
CPC .......................... A61K 31/7088; A61K 48/00
See application file for complete search history.

(56) References Cited

U.S. PATENT DOCUMENTS

| 5,834,306 | A | 11/1998 | Webster |
| 6,893,867 | B1 | 5/2005 | Webster |
| 2005/0266549 | A1 | 12/2005 | Webster |
| 2013/0236433 | A1 | 9/2013 | Webster |
| 2015/0139952 | A1 | 5/2015 | Webster |
| 2015/0322410 | A1 | 11/2015 | Webster |

OTHER PUBLICATIONS

Dor et al (The EMBO Journal, 21(8): 1939-1947, 2002).*
Gupta et al (Circ Res. 2009;105:724-736).*
Webster et al., "Optimized therapeutic angiogenesis for peripheral ischemia using stem cells transducted with an ischemia-regulated conditionally silenced AAV," Circulation (2005) 111(13): 1721, col. 2, para 2. Abstract No. 5008.
European Search Report and Search Opinion dated Jan. 14, 2013 for European Patent Application No. 10827598.9, filed May 29, 2012.
Webster, et al., Combination cell and gene therapy for peripheral ischemia using myoblasts and stem cells engineered with conditionally silenced genes, Miami 2006 Winder Symposium—Interpreting the Human Genome Jan. 24-28, 2006.
Spiga, et al., Delivery of VEGF165 with hypoxia-regulated adeno-associated virus (AAV) serotype 9 produces stable conduction vessels in mouse ischemic limbs, Miami 2006 Winter Symposium—Interpreting the Human Genome, Jan. 24-28, 2006.
Dougherty, et al., Robust hypoxia-selective regulation of a retinal pigment epithelium-specific adeno-associated virus vector, Molecular Vision, 2008: 14: 471-480.
Balasubramanian et al., "Morphine sulfate inhibits hypoxia-induced vascular endothelial growth factor expression in endothelial cells and cardiac myocytes", J Mol Cell Cardiol (2001) 33: 2179-2187.
Barkefors et al., "A fluidic device to study directional angiogenesis in complex tissue and organ culture models", Lab on a Chip (2009) 9(4): 529-535.
Forsythe et al., "Activation of vascular endothelial growth factor gene transcription by hypoxia-inducible factor 1", Molecular and Cellular Biology (1996) 16(9): 4604-4613.
Laitakari, "Size, shape, structure, and direction of angiogenesis in laryngeal tumour development", J Clin Pathol. (Apr. 2004) 57(4): 394-401.
Levy et al., "Transcripted regulation of the rat vascular endothelial growth factor gene by hypoxia", J Biol Chem (Jun. 2, 1995) 270(22): 1333-13340.
Liu et al., "Hypoxia regulates vascular endothelial growth factor gene expression in endothelial cells", Circulation Research (1995) 77: 638-643.
Milkiewicz et al., "Vascular endothelial growth factor mRNA and protein do not change in parallel during non-inflammatory skeletal muscle ischaemia in rat", J Physiol (2006) 577(2): 671-678.
Wintermantel et al., "Angiopolarity of cell carriers: Directional angiogenesis in resorbable liver cell transplantation devices", Angiogenesis: Key Principles—Science—Technology—Medicine (1992): 331-334.
Invitation to Pay Additional Fees for PCT/US2010/054929 mailed Mar. 25, 2011.
International Search Report and Written Opinion for PCT/US2010/054929 mailed Jun. 10, 2011.
International Preliminary Report on Patentability for PCT/US2010/054929 mailed May 10, 2012.

* cited by examiner

*Primary Examiner* — Deborah Crouch
*Assistant Examiner* — Magdalene Sgagias
(74) *Attorney, Agent, or Firm* — Wolf, Greenfield & Sacks, P.C.

(57) ABSTRACT

Methods and compositions for the treatment of hypoxia associated disorders by directional angiogenesis/arteriogenesis. Conditionally silenced vectors expressing a therapeutic molecule under hypoxic conditions avoid chaotic vascularization and allow for the orderly growth of new vessels into damaged tissue.

9 Claims, 10 Drawing Sheets

Figures 10A-10C
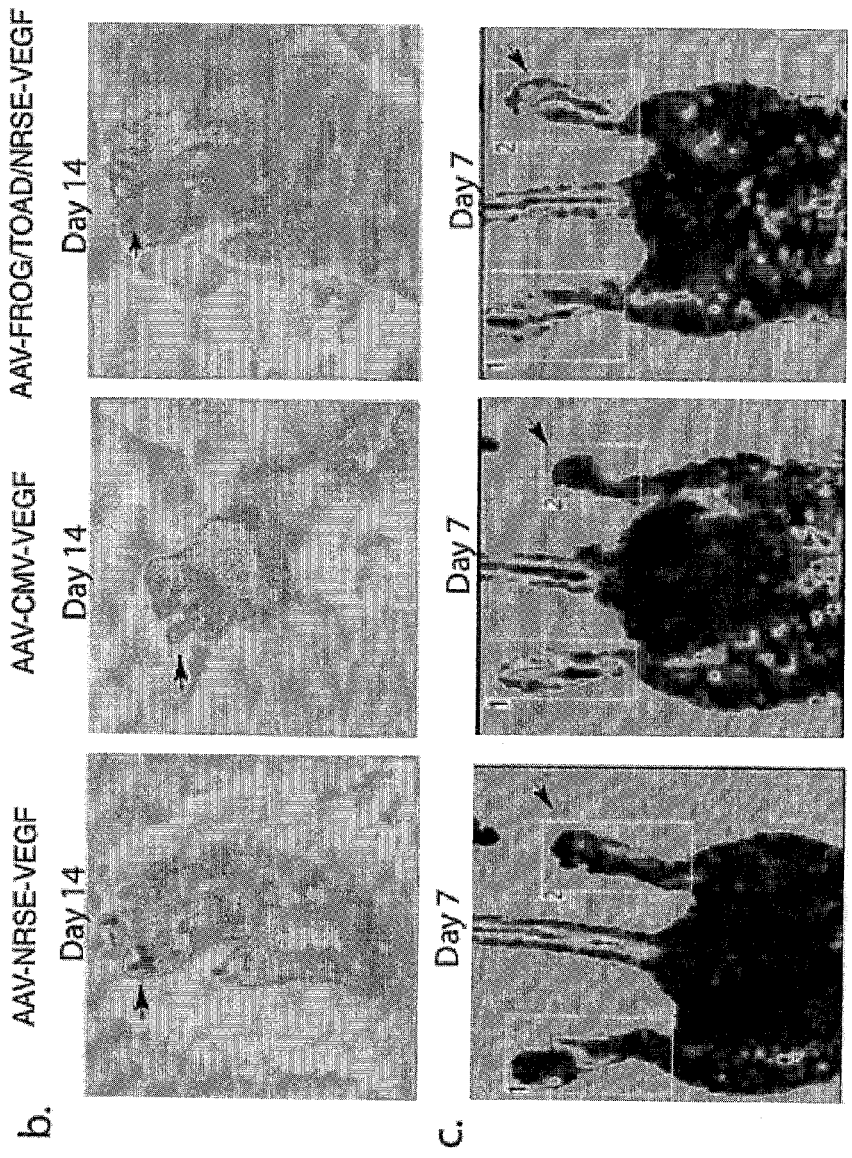

SEQUENCE LISTING

<160> NUMBER OF SEQ ID NOS: 6

<210> SEQ ID NO 1
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ccggctcttc cagagcaagg caaccacagg agaccctgtc acgtcctgca cgacctcttc      60
cagagcaagg caaccacagg agaccctgtc acgtcctgca cgacctcttc cagagcaagg    120
caaccacagg agaccctgtc acgtcctgca cgac                                154

<210> SEQ ID NO 2
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ccgggtcgtg caggacgtga cagggtctcc tgtggttgcc ttgctctgga agaggtcgtg      60
caggacgtga cagggtctcc tgtggttgcc ttgctctgga agaggtcgtg caggacgtga    120
cagggtctcc tgtggttgcc ttgctctgga agag                                154

<210> SEQ ID NO 3
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ccggggtgtg catttagcta aattccccac tgtcacgtcc tgcacgacgg tgtgcattta      60
gctaaattcc ccactgtcac gtcctgcacg acggtgtgca tttagctaaa ttccccactg    120
tcacgtcctg cacgac                                                    136

<210> SEQ ID NO 4
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccgggtcgtg caggacgtga cagtggggaa tttagctaaa tgcacaccgt cgtgcaggac      60
gtgacagtgg ggaatttagc taaatgcaca ccgtcgtgca ggacgtgaca gtggggaatt    120
tagctaaatg cacacc                                                    136

<210> SEQ ID NO 5
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 5
ccggctcttc cagagcaagg caaccacagg agaccctgtc acgtcctgca cgacggtgtg      60
catttagcta aattccccac tgtcacgtcc tgcacgacct cttccagagc aaggcaacca     120
caggagaccc tgtcacgtcc tgcacgacgg tgtgcattta gctaaattcc ccactgtcac    180
gtcctgcacg ac                                                         192

<210> SEQ ID NO 6
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
ccgggtcgtg caggacgtga cagtggggaa tttagctaaa tgcacaccgt cgtgcaggac      60
gtgacagggt ctcctgtggt tgccttgctc tggaagaggt cgtgcaggac gtgacagtgg     120
ggaatttagc taaatgcaca ccgtcgtgca ggacgtgaca gggtctcctg tggttgcctt    180
gctctggaag ag                                                         192
```

FROG/TOAD CONDITIONALLY SILENCED VECTORS FOR HYPOXIA GENE THERAPY

CROSS REFERENCE TO RELATED APPLICATIONS

This application is a §371 national phase entry of International Application No. PCT/US10/054929, filed Nov. 1, 2010, which claims priority to U.S. provisional application No.: 61/256,381, filed Oct. 30, 2009, the entire contents of which are incorporated herein by reference.

GOVERNMENT FUNDING

This invention was made with government support under grant number RO1 HL072924 awarded by the National Institutes of Health. The government has certain rights in the invention.

FIELD OF THE INVENTION

Embodiments of the invention comprise methods of treating hypoxia and associated conditions. In particular, directional therapeutic angiogenesis induced in patients via a conditionally silenced vector expressing a desired factor.

BACKGROUND

Therapeutic angiogenesis is a procedure developed for the treatment of ischemia whereby new blood vessels are induced to grow in ischemic tissue in response to exogenous angiogenic growth factors delivered by genes or cells. The main clinical targets are myocardial and critical limb ischemia caused respectively by coronary and peripheral artery disease. Persuasive preclinical results of both gene and precursor stem cells lead to a series of Phase II/III clinical trials. These have been only moderately successful, revealing safety of the procedures but minimal efficacy.

SUMMARY

This Summary is provided to present a synopsis of the invention to briefly indicate the nature and substance of the invention. It is submitted with the understanding that it will not be used to interpret or limit the scope or meaning of the claims.

Preferred embodiments comprise vectors that promote directional arteriogenesis which is selectively and in some embodiments, exclusively driven by hypoxia-regulated conditionally silenced AAV vectors. These compositions provide for more rapid and efficient revascularization and tissue salvage by tight hypoxia-regulation for growth factor expression by combinations of NRSE and TOAD/FROG silencer elements. Methods are provided wherein conditional silencing of growth factor gene expression provides directional arteriogenesis in a manner that is determined by the degree of conditional silencing. This produces efficient revascularization of ischemic tissue that is also determined by the degree of conditional silencing.

In other preferred embodiments, the vectors comprise FROG/TOAD and NRSE silencers that confer tight regulation by hypoxia and more rapid revascularization with maximal responses effected by a combination of 3 silencer elements (NRSE/FROG/TOAD). This unexpected property of 3 heterogeneous silencer elements may be attributed to silencing of gene expression in a broad range of different cell types compared to NRSE alone wherein silencing is restricted to non-neuronal cells and may function poorly or not at all in stem cells.

In other preferred embodiments, the use of a combination of gene regulatory elements to selectively express pro-angiogenic genes in ischemic tissues in skeletal and cardiac muscles comprising a permanent delivery gene therapy vector such that regulated expression of the gene promotes the generation of stable mature blood vessels that cause muscle reperfusion.

In another preferred embodiment, the regulatory system delivers genes to target cells comprising skeletal and cardiac myocytes, endothelial cells, smooth muscle cells, pericytes, stem cells, etc.

Other aspects are described infra.

BRIEF DESCRIPTION OF THE DRAWINGS

FIG. 1A is a schematic representation showing the conditional silencing of gene expression is operated by the interaction between NRSE histone deacetylase activity and HIF-1 histone acetyltransferase activity. FIGS. 1B-1D show gene regulation by conditional silencing. FIGS. 1B-1C: cardiac myocytes, HeLa cells or C2-C12 skeletal myocytes were co-transfected with AAV shuttle vectors as indicated and Renilla luciferase as an internal control. 24 hours after transfections, the cultures were incubated under aerobic or hypoxic (0.5%-1% $O_2$) atmosphere for an additional 24 hours and harvested for luciferase expression. FIG. 1D: C2C12 myocytes were infected with AAV-GFP directed by PGK or CS-PGK and exposed to air or hypoxia as indicated. FIG. 1E: C2C12 myocytes were infected with AAV-VEGF directed by PGK or CS-PGK and exposed to air or hypoxia, secreted VEGF was measured in media at 24 h by ELISA.

FIG. 3A: ischemia was induced in the hind limbs of mice and the indicated vectors were delivered by intramuscle injection after surgery. Weekly Doppler scans were implemented on the limbs up to 12 weeks and then monthly with 12 mice per group. Mice were sacrificed at each time point and muscles processed for RT-PCR to quantify hVEGF or fixed and paraffin embedded for immunostaining. Squared (top curve) AAV-CS-VEGF: circles and triangles (bottom curves) Adenovirus (Ad) low and high dose. All limbs with Ad-VEGF auto-amputated; yellow arrow indicates flow in a 6-month salvaged AAV limb. FIG. 3B: VEGF expression was quantified by RT-PCR in limb muscle at the indicated times (n=3). FIG. 3C: hind limb reperfusion comparing AAV-CS-VEGF (green) with AAV-PGK-VEGF (red) and PBS (lower curves). Methods as in FIG. 3A; both AAV vectors restored flow, but flow was restored more rapidly by CS-VEGF.

Figures 5A, 5B, 5C, 5D:
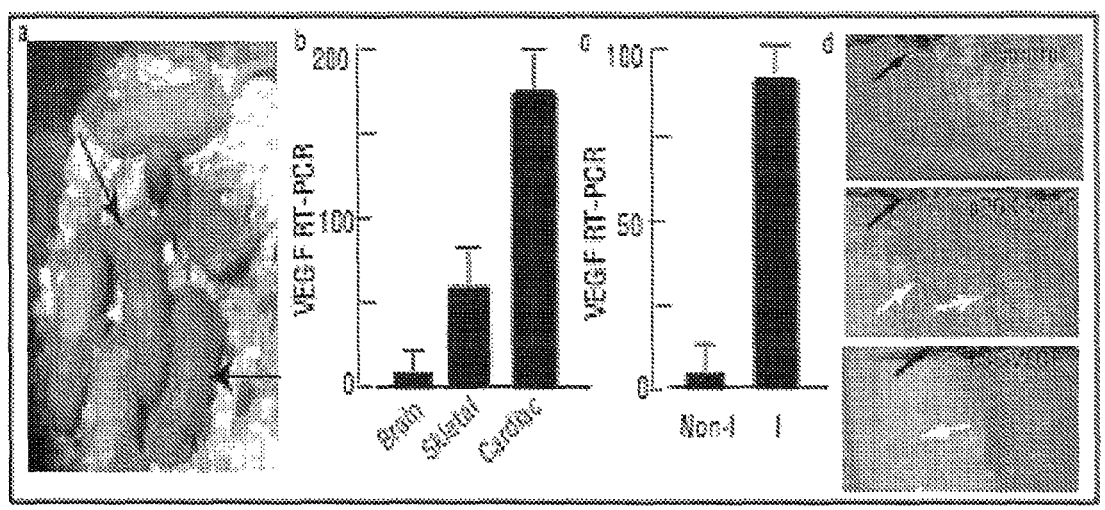

FIGS. 5A-5D show gene regulation by conditional silencing in vivo. One day old mice (FIG. 5A) were given interocular injections of AAV9-PGK-VEGF or AAV9-CS-VEGF (FIG. 5B). In FIG. 5A, one hind limb of 4 week old mice was made ischemic by ligation and dissection of the femoral artery and tissues were harvested from the ischemic and non-ischemic contralateral limbs and VEGF measured by RT-PCR. In FIG. 5D, rat foot pads were injected with plasmid vectors expressing PGK-VEGF or CS-PGK-VEGF and examined for new vessel growth after 4 weeks. Black arrows indicate position of sutures placed at the time of DNA delivery to mark the area of interest. White arrows indicate new vessels generated in response to the PGK but not the CS vector.

Figure 6:
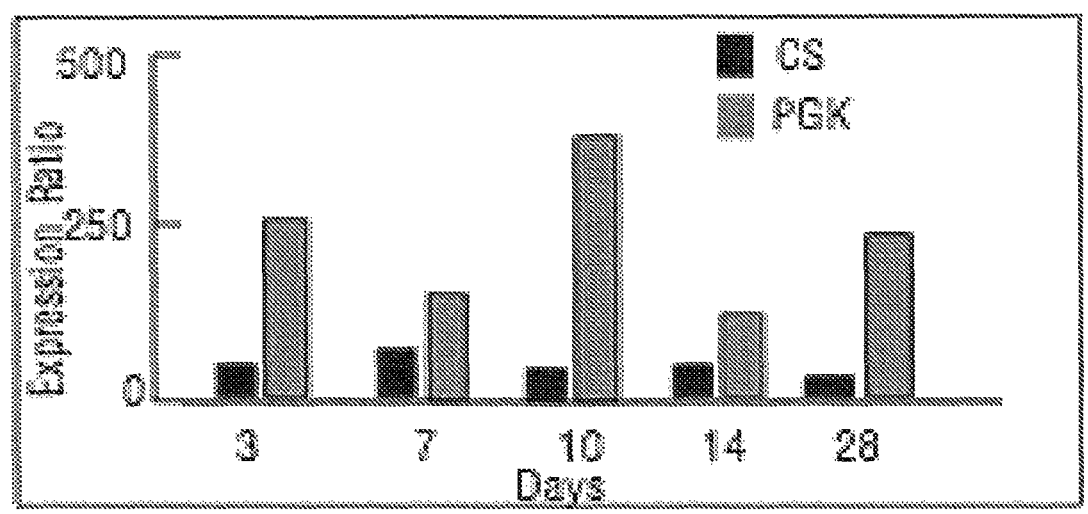

FIG. 6 is a graph showing the VEGF:HEY2 ratio during early angiogenesis. Ischemic hindlimbs were treated with AAV9-VEGF driven by low regulation (PGK) or conditionally silenced (CS) promoters. Human VEGF and mouse HEY2 expression were measured by RT-PCR in muscles harvested at the indicated time points (n=2). The mean VEGF expression during this period was 6.2 fold higher in the muscles treated with PGK versus CS vector indicating that basal and as well as induced expression are lower in the CS vectors.

Figures 7A, 7B, 7C:
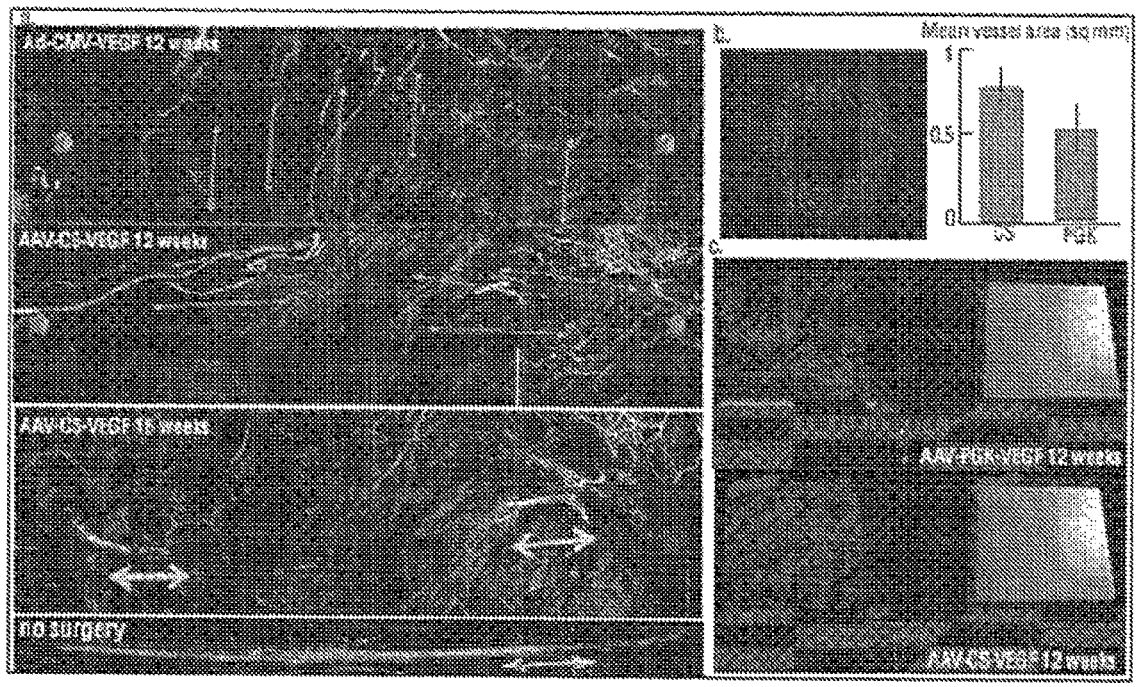

FIGS. 7A-7C show vessel orientation and density during Ad or AAV9-CS-VEGF treatments. FIG. 7A shows hind limb muscle sections stained with DiI and imaged by confocal dual photon fluorescence microscopy. Red circles with X indicate position of sutures used to tie the femoral artery and mark the region of ischemia. In 12 week Ad treatment groups, capillaries preferentially grow vertical to the plane of the femoral artery as indicated by green double arrows. Yellow double arrows depict large arteries in the ischemic region in the AAV-CS-VEGF group. FIG. 7B shows a section through an artery stained with SMA antibody and Dapi. Vessel areas were quantitated on >50 SMA-positive vessels per condition using Area Trace software. FIG. 7C: capillary density was quantified on confocal sections of DiI stained vessels using Volocity Image software.

Figures 8A, 8B, 8C:
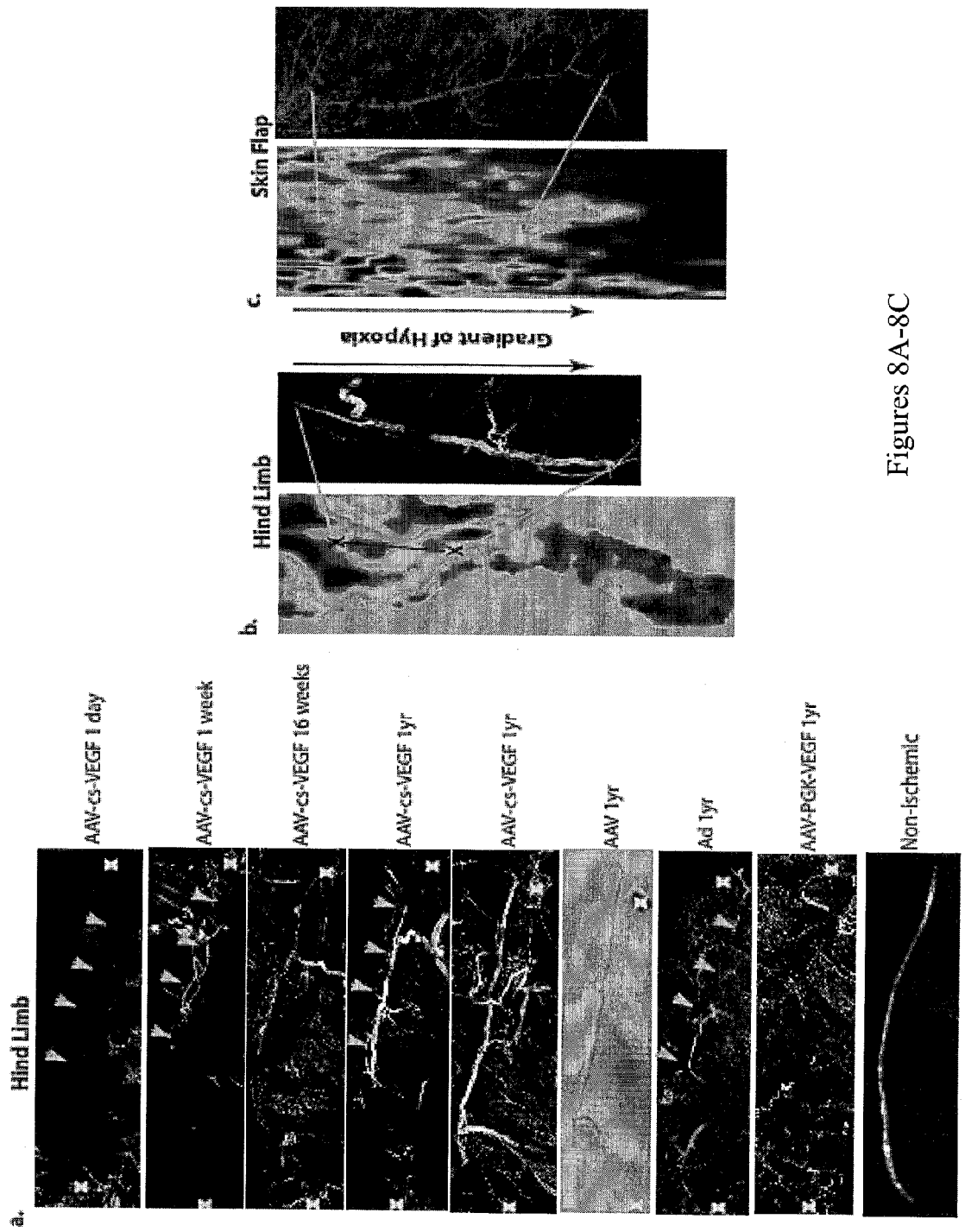

FIGS. 8A-8C show directional arteriogenesis in the femoral tract. FIG. 8A shows representative DiI-stained muscle sections taken at the indicated times after ischemia with the indicated treatments. Each time point is representative of at least 3 mice per panel. White crosses indicate position of femoral sutures enclosing the region of femoral excision; yellow arrowheads denote position of the femoral tract (where the femoral artery was excised but femoral nerve remains). A large artery with dimensions similar to the normal femoral artery is visualized within the femoral tract at 1-year in both AAV-CS-VEGF treatments but not in Ad-CMV-VEGF, AAV-PGK-VEGF or AAV-CMV treatments (AAV-CMV not shown). FIGS. 8B and 8C show the relationships between blood flow, ischemia and vessel growth in hind limb (FIG. 8B) and skin flap (FIG. 8C) models. FIG. 8B: Left panel depicts a Doppler scan of a reperfused hind limb, the connected black crosses mark the position of the excised femoral and the right panel shows a regenerated artery situated within the femoral tract. FIG. 8C: Left panel indicates a Doppler image of skin flap during recovery from ischemia with gene therapy vector delivered to the ischemic region; right panel shows a parallel DiI-stained vessel growing down the gradient of hypoxia towards the region of greatest ischemia also in this model.

Figures 9A, 9B, 9C, 9D:
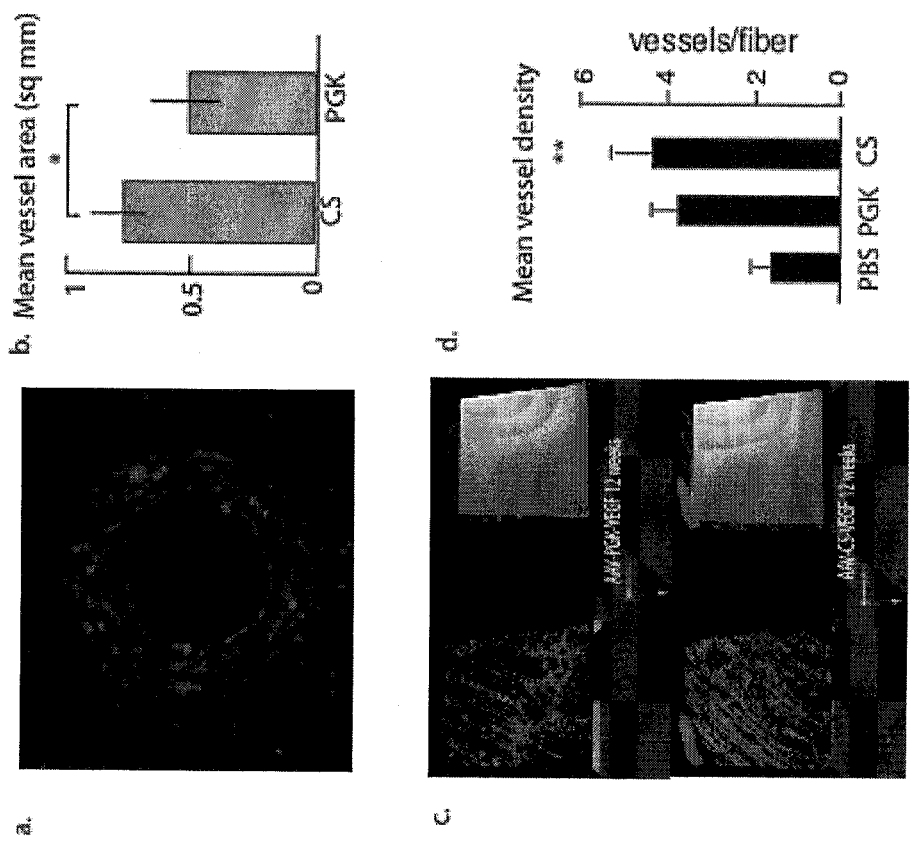

FIGS. 9A-9D show the therapeutic arteriogenesis by conditional silenced VEGF. FIGS. 9A and 9D: Mouse hind limbs were injected with $10^8$ genomes of the AAV-CS-VEGF OR AAV-unreg/PGK-VEGF and the muscles harvested after 16 weeks. Muscle sections were stained with anti-smooth muscle actin (to identify arterioles and arteries) and Dapi (FIG. 9A) and the mean volumes of vessels (FIG. 9B) were quantified. Briefly, the area of each of the 10 largest vessels in each of 4 slides were measured with the trace tool of Axiovision software. The vessel areas in each limb were counted in at least 3 different sections from the thigh area in cross section to obtain a mean for each animal ($p<0.01$). FIGS. 9C and 9D: Vessel densities were quantified using Volocity software on confocal images. Vessel volume data was generated using a uniform region of interest for each field of view. 10 fields of view from 3 separate mice were used to evaluate mean vessel density (volume of total DiI stained vessels) for each treatment ((FIG. 9B): $p<0.05$). Vessel density was confirmed by counting $CD31^+$ stained sections.

FIGS. 10A-10C show the optimal tissue salvage and revascularization by combined FROG/TOAD/NRSE-mediated conditional silencing. FIG. 10A is a schematic of an embodiment of the optimized vector. FIG. 10B shows a comparison of toe salvage by AAV vectors on Day 14 following ischemia and gene therapy. Limbs treated with AAV-NRSE-VEGF had 3 out of 12 necrotic toes; limbs treated with AAV-CMV-VEGF lost all toes within 2 weeks and displayed advanced auto-amputation; limbs treated with FROG/TOAD/NRSE-VEGF had no necrosis and 100% toe and limb salvage. FIG. 10C: Doppler analyses at 7 days showed minimal blood flow in ischemic limbs treated with AAV-NRSE-VEGF, no flow and initiation of autoamputation in limbs treated with AAV-CMV-VEGF but significantly recovered flow in limbs treated with AAV-FROG/TOAD/NRSE-VEGF ($p<0.05$; n=3). Methods: Ischemia was induced in the hind limbs of mice and the indicated vectors were delivered i.m. after surgery. Toes were examined and photographed daily; Doppler scans were implemented twice per week. All limbs treated with AAV-CMV-VEGF auto-amputated within 1-month; no auto-amputations were observed in the other AAV groups. Arrows in FIG. 10C indicate ischemic limbs.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Similarly, all genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Ischemia" is defined as an insufficient supply of blood to a specific organ or tissue. A consequence of decreased blood supply is an inadequate supply of oxygen to the organ or tissue (hypoxia). Prolonged hypoxia may result in injury to the affected organ or tissue. "Anoxia" refers to a virtually complete absence of oxygen in the organ or tissue, which, if prolonged, may result in death of the organ or tissue.

"Hypoxic condition" is defined as a condition under which a particular organ or tissue receives an inadequate supply of oxygen.

"Anoxic condition" refers to a condition under which the supply of oxygen to a particular organ or tissue is cut off.

"Reperfusion" refers to the resumption of blood flow in a tissue following a period of ischemia.

"Ischemic injury" refers to cellular and/or molecular damage to an organ or tissue as a result of a period of ischemia and/or ischemia followed by reperfusion.

As used herein, the term "injury" is to be interpreted broadly to include any impact on a cell, tissue, or organ that results in an undesirable consequence to the cell, tissue, or organ. In some embodiments, an injury results from an insult that is observable or otherwise definable, but the ability to identify the source of the injury is not limiting. Thus, in some embodiments an injury comprises an ischemic injury. However, in some embodiments injury can include injuries subsequent to which a cell, tissue, and/or organ exhibits an impaired function that is secondary to one or more causes, identifiable or not, other than ischemic injury.

"Pro-angiogenic" refers to stimulating growth of new blood vessels, of either microvessels of less than 100 μM in diameter or larger and more muscular blood vessels.

As used herein, the term "aberrant vascularization" or "aberrant angiogenesis" or "chaotic growth" will be understood to include abnormal neovascularization, including the formation of new blood vessels, larger blood vessels, more branched blood vessels (intussusception), and any and all mechanisms that lead to inappropriate or increased blood carrying capacity to a diseased tissue or site.

As used herein, "directional growth" refers to the growth of vessels in (a) controlled direction(s) from a desired point to a desired point. For example, hypoxia dictated directional vessel growth in a soft tissue ischemia model by creating gradients of growth factors (VEGF, SDF-1) that provide cues for EPC homing and presumably endothelial cell sprouting down the gradient. The data herein also show directional vessel growth and possibly involving shear stress generated as vessel networks make connections upstream and downstream of the region of an excised femoral artery and blood flow resumes from hip to ankle.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, in vivo amounts, etc.).

As used herein, "cell-permeant DNA or RNA vector" is a vector that can be taken up by a cell with or without transfection agents. For example, many viral sequences encode for cell binding glyco-proteins, or they have regions allowing for intracellular targets. Other examples include nucleic acid sequences which allow for the efficient intra-cellular transformation by the vector.

Treatment of Diseases or Disorders

Preclinical gene and cell therapy models focused exclusively on angiogenesis, hence the term "therapeutic angiogenesis". These studies have two major flaws (1) inadequate delivery vehicles that extinguished gene expression too early (2) delivery of unregulated, constitutively active genes that did not provide directional cues for new vessel growth. These flaws were largely masked by therapeutic time courses that were too short, and analyses of vessel growth that were restricted to unidimensional quantification of capillary density.

In a preferred embodiment, a method for promoting directional angiogenesis in vivo comprising administering to a patient, a composition comprising an adeno-associated viral (AAV) vector wherein pro-angiogenic gene expression is regulated by a promoter such as for example, a phosphoglycerate kinase (PGK) promoter, in conjunction with a combined cassette of hypoxia response elements (HREs) and silencer elements that confers silencing of gene expression under aerobic conditions and activation of expression by ischemia. Such vectors have been described in U.S. Pat. No. 5,834,306 which is incorporated herein by reference in its entirety.

In preferred embodiments, administration of a pro-angiogenic growth factor gene (such as, for example, vascular endothelial growth factor (VEGF)) in a semi-permanent, tissue-specific (for example, muscle-tropic) AAV9 vector driven by a hypoxia-regulated promoter induces or promotes directional angiogenesis followed by arteriogenesis and re-establishment of a functional vascular network with stable tissue reperfusion. Examples of pro-angiogenic factors comprise at least one of: endothelial growth factor, fibroblast growth factor (FGF), platelet derived growth factor (PDGF), insulin-like growth factor (IGF), epidermal growth factor (EGF), transforming growth factor (TGF), hepatocyte growth factor, proliferin, angiotropin, angiopoietin, vascular endothelial growth factor (VEGF), transforming growth factor-beta (TGF-beta), or erythropoietin (EPO).

Other examples of factors that can be expressed from the conditionally silenced vectors include for example, c-kit ligand/stem cell factor, insulin, insulin like growth factor-1 (IGF-1), nerve growth factor (NGF), bone morphogenetic protein (BMP), leukemia inhibitory factor (LIF), flt-1 ligand, brain derived neurotrophic factor (BDNF), interleukins such as but not limited to interleukin 3 (IL-3), interleukin 6 (IL-6), interleukin 7 (IL-7), and interleukin 13 (IL-13), stromal derived factor (SDF), stem cell factor (SCF), granulocyte colony stimulating factor (G-CSF), and matrix metallo-proteinase (MMP) inhibitors.

As used herein, "conditional silencing" is meant as the use of "gene silencer elements" including but not limited to NRSE, FROG, TOAD and conditionally inducible elements including but not limited to hypoxia response elements (HREs), inflammatory response elements (IREs) and shear-stress activated elements (SSAEs).

In a preferred embodiment, a conditional silencer comprises NRSE, FROG, TOAD, NRSE/FROG/TOAD, FROG/TOAD or combinations thereof. Examples include:

TOAD/PGK (Sense)
(SEQ ID NO: 1)
5'-CCGGCTCTTCCAGAGCAAGGCAACCACAGGAGACCCTGTCACGTCCT

GCACGACCTCTTCCAGAGCAAGGCAACCACAGGAGACCCTGTCACGTCCT

GCACGACCTCTTCCAGAGCAAGGCAACCACAGGAGACCCTGTCACGTCCT

GCACGAC-3'

(Antisense)
(SEQ ID NO: 2)
3'-GAGAAGGTCTCGTTCCGTTGGTGTCCTCTGGGACAGTGCAGGACGTG

CTGGAGAAGGTCTCGTTCCGTTGGTGTCCTCTGGGACAGTGCAGGACGTG

CTGGAGAAGGTCTCGTTCCGTTGGTGTCCTCTGGGACAGTGCAGGACGTG

CTGGGCC-5'

FROG/PGK (Sense)
(SEQ ID NO: 3)
5'-CCGGGGTGTGCATTTAGCTAAATTCCCCACTGTCACGTCCTGCACGA

CGGTGTGCATTTAGCTAAATTCCCCACTGTCACGTCCTGCACGACGGTGT

GCATTTAGCTAAATTCCCCACTGTCACGTCCTGCACGAC-3'.

(Antisense)
(SEQ ID NO: 4)
3'-CCACACGTAAATCGATTTAAGGGGTGACAGTGCAGGACGTGCTGCCA

CACGTAAATCGATTTAAGGGGTGACAGTGCAGGACGTGCTGCCACACGTA

AATCGATTTAAGGGGTGACAGTGCAGGACGTGCTGGGCC-5'.

FROG-TOAD/PGK (Sense)
(SEQ ID NO: 5)
5'-CCGGCTCTTCCAGAGCAAGGCAACCACAGGAGACCCTGTCACGTCCT

GCACGACGGTGTGCATTTAGCTAAATTCCCCACTGTCACGTCCTGCACGA

CCTCTTCCAGAGCAAGGCAACCACAGGAGACCCTGTCACGTCCTGCACGA

CGGTGTGCATTTAGCTAAATTCCCCACTGTCACGTCCTGCACGAC-3'.

(Antisense)
(SEQ ID NO: 6)
3'-GAGAAGGTCTCGTTCCGTTGGTGTCCTCTGGGACAGTGCAGGACGTG

CTGCCACACGTAAATCGATTTAAGGGGTGACAGTGCAGGACGTGCTGGAG

AAGGTCTCGTTCCGTTGGTGTCCTCTGGGACAGTGCAGGACGTGCTGCCA

CACGTAAATCGATTTAAGGGGTGACAGTGCAGGACGTGCTGGGCC-5'.

In a preferred embodiment, a conditional silencer comprises at least one of nucleotide sequences set forth as SEQ ID NOS: 1 to 6, derivatives, variants, mutants or homologs thereof.

In another preferred embodiment, a conditional silencer comprises NRSE, FROG, TOAD, FROG/TOAD or combinations thereof.

The conditional silencers used in the various vectors described in the embodiments have been found to be superior to any current vectors. For example, (1) AAV9-PGK-VEGF does not promote directional vessel growth despite being hypoxia-regulated-because of high (unsilenced) basal normoxic expression—effects that are worsened in AAV9-CMV-VEGF; (2) AAV9-CMV-VEGF causes random vessel growth and no limb salvage, 100% auto-amputation—worse than no treatment; (3) Insertion of FROG/TOAD provides tighter regulation providing the best therapy with more rapid angiogenesis and 100% toe salvage despite lower gene expression compared with AAV9-CS(NRSE)-VEGF (see, for example, FIGS. 10A-10C). Without wishing to be bound by theory, may be due to a better VEGF:Notch ratio. The inclusion of FROG/TOAD and the graded response to conditional silencing was unexpected and surprising. For example, the results obtained regarding the toe salvaging, the more rapid doppler recovery with the FROG/TOAD could not have been predicted.

In another preferred embodiment, conditionally inducible elements comprising: hypoxia response elements (HREs), inflammatory response elements (IREs), shear-stress activated elements (SSAEs), metal responsive elements (MREs) or combinations thereof.

In another preferred embodiment, a conditionally silenced vector, conditionally expresses factors comprising at least one of: endothelial growth factor, fibroblast growth factor (FGF), platelet derived growth factor (PDGF), insulin-like growth factor (IGF), epidermal growth factor (EGF), transforming growth factor (TGF), hepatocyte growth factor, proliferin, angiotropin, angiopoietin, vascular endothelial growth factor (VEGF), transforming growth factor-beta (TGF-beta), insulin like growth factor-1 (IGF-1), nerve growth factor (NGF), stromal derived factor (SDF), stem cell factor (SCF), or erythropoietin (EPO).

In another preferred embodiment, a conditionally silenced vector comprises: an adeno-associated viral (AAV) vector, a pro-angiogenic factor and/or growth factor and/or cellular migration factor, a promoter, a combined cassette of hypoxia response elements (HREs) and silencer elements.

In one preferred embodiment, vector gene expression is inhibited (conditionally silenced) under aerobic conditions and activated by ischemic conditions.

In a preferred embodiment, the methods of treating a disease or disorder associated with hypoxia comprises the transfer of a pro-angiogenic factor, for example, the VEGF gene, using a semi-permanent gene delivery vehicle such as an adeno-associated viral (AAV) vector or, a lentiviral vector wherein VEGF expression is regulated by a promoter, such as, for example, a phosphoglycerate kinase (PGK) promoter with a combined cassette of hypoxia response elements (HREs) and silencer elements that confers silencing of gene expression under aerobic conditions and activation of expression by ischemia ("conditionally silenced").

In preferred embodiments, the conditionally silenced vectors expressing pro-angiogenic factors and/or other factors are administered to patients at risk of developing or suffering from muscle ischemia including peripheral and myocardial ischemia, hindlimb ischemia, retinal ischemia, cancer, heart disease, stroke, macular degeneration, diabetic retinopathy, arthritis, the crown of balding subjects to enhance hair graft during transplant, and the like.

In another preferred embodiment, a method of producing controlled directional growth of blood vessels comprises administering to a patient in need thereof, a conditionally silenced vectors expressing pro-angiogenic and/or other factors whereby the vector produces a therapeutically effective controlled amount of pro-angiogenic growth factors in target tissues. The controlled amount of pro-angiogenic factor produced prevents the chaotic growth of vessels into damaged tissue.

The conditionally silenced vectors of the invention are beneficially used for the treatment of injured cells or tissues in numerous different medical conditions. A non-limiting list of injuries include structural tissue injury, such as cartilage and meniscal damage, ischemic injury, including that connected to stroke, myocardial infarction, heart attack, spinal cord injury, donor organ injury, organ transplant recipient, reperfusion, vascular stenting, transient ischemic attack, chronic and acute mesenteric ischemia, claudication, critical limb ischemia, cancer, bone marrow injuries and renal damage. Diseases that can be treated or prevented using the compositions of the invention, comprise: diabetes, cancer, cardiovascular diseases or disorders, autoimmunity, neurological diseases or disorders, inflammation and the like.

In yet another embodiment, conditionally silenced vectors of the invention may be administered to a subject before, during or after injury and ischemic injury. Ischemic injury is generally caused by an occlusive event in the blood vessel supplying the tissue. When the vessel opens up, or is reopened through therapeutic intervention, often further damage is created in the tissue by the influx of not only scar-forming cells, but also inflammatory cells which release destructive enzymes (reperfusion injury).

The conditionally silenced vectors expressing pro-angiogenic factors and/or other factors may be administered to a stroke, heart attack or spinal cord injury victim in order to reduce the severity of cell and tissue loss during the post-ischemic event period. These compositions can be administered before, during and/or after any medical procedures that carry risk of reperfusion injury during revascularization procedures, such as placement of a stent after myocardial ischemia, coronary bypass grafting, and organ transplantation of heart, liver, lung, pancreas and kidney. In each of these cases, the composition is preferably administered intravenously either distant or local to the site of revascularization and resulting in directional growth of vessels.

Repeated bouts of ischemia and reperfusion injury are thought to be a factor leading to the formation and failure to heal of chronic wounds, such as pressure sores and diabetic foot ulcers. Accordingly, chronic wounds may be treated by administering a composition of the invention.

A patient undergoing intestinal surgery may be treated with the inventive composition prior to, contemporaneously with and/or after blood flow is restored to the intestine, in order to preclude or reduce reperfusion injury.

The composition of the invention also is useful in conditioning organs and tissues undergoing preparation for transplant. In one embodiment, a donor heart may be contacted with the inventive tissue repair compositions before, during, and/or after implantation such that injury, including, without limitation, reperfusion injury, is reduced in the period after transplant. The recipient of the transplant may also be treated with the compositions, before, during and/or after the transplantation.

Methods of the present invention are also useful to prevent tissue damage and/or death, due to ischemia and/or subsequent reperfusion, in a variety of tissues. An exemplary application is in the reduction of damage due to recurrent myocardial ischemia following a heart attack. The expression of therapeutic genes in the cardiac tissue of heart attack victims may decrease the risk of injury to the tissue during any subsequent ischemic episodes.

Similarly, subjects who have been diagnosed with transient cerebral ischemia, blood clots or other risk factors for stroke may benefit from the use of hypoxia-inducible brain-specific constructs. Subjects diagnosed with acute or chronic renal failure are at greater risk for further ischemic damage to the kidneys. Such subjects may benefit from a therapeutic gene under the control of a kidney-specific promoter, expression of which is enhanced by hypoxic conditions. A variety of other tissues diagnosed as "at risk" for ischemia may be similarly protected, as will be appreciated by one of skill in the art having the benefit of the present specification.

In other preferred embodiments, the conditionally silenced vectors expressing pro-angiogenic and/or other factors can be administered in conjunction either separately or as part of a treatment regimen. Such drugs which are particularly well suited for the reduction of ischemic injury following acute myocardial infarction or other ischemic injuries include, but are not limited to, vasodilators such as adenosine, dipyridamole and cilostazol; nitric oxide donors; prostaglandins and their derivatives; antioxidants including hydroxyflavonols and dihydroxy; membrane stabilizing agents; anti-TNF compounds; anti-inflammatories including dexamethasone, aspirin, pirfenidone, meclofenamic acid, and tranilast; hypertension drugs including beta blockers, ACE inhibitors, and calcium channel blockers; anti-metabolites such as 2-CdA; vasoactive substances including vasoactive intestinal polypeptides (VIP); insulin; protein kinases; antisense oligonucleotides including resten-NG; immunosuppressants including sirolimus, everolimus, tacrolimus, etoposide, cyclosporins such as cyclosporine A and mitoxantrone; anti-thrombins; antiplatelet agents including tirofiban, eptifibatide, and abciximab; cardio protectants including pituitary adenylate cyclase-activating peptide (PACAP), apoA-I milano, amlodipine, nicorandil, cilostaxone, and thienopyridine; anti-leukocytes; cyclooxygenase inhibitors including COX-1 and COX-2 inhibitors; peptidose inhibitors which increase glycolitic metabolism including omnipatrilat; calcium sensitizers including lerosimendan, semidan and pimobendan. Protein or peptide drugs can be human, non-human, recombinant or synthetic and can be the full length native form or an active fragment thereof.

In one embodiment, the conditionally silenced vectors which are suited for the treatment of ischemic injury are delivered at or near the site of a reopened occlusion following myocardial infarction or other acute ischemic syndromes. The delivery of the vector compositions at or near the site of the previous occlusion allows the drugs to be delivered by the blood flow downstream to the reperfused tissue. The vector compositions can be delivered by a stent containing drugs in openings in the stent as described above. The vector compositions can also be delivered by a drug coated stent, an implant, microspheres, a catheter, coils, or other local delivery means. For example, microspheres, coils, liposomes, or other small drug carriers can be delivered locally at or near the site of a previous occlusion with a catheter or drug delivery stent. These small drug carriers are released and pass downstream into the myocardium where they may implant themselves delivering the drug directly to the ischemic tissue.

The stent for delivery of the compositions may be placed within or adjacent another previously placed stent. The implantation site for the stent may be at or near the site of the occlusion. An implantation site may also be selected at or near a location of a plaque rupture site or a vessel narrowing.

In another embodiment, the local delivery of the vectors the directional controlled growth of vessels is used in combination with the systemic delivery of another therapeutic agent, such as an anti-ischemic agent. Alternatively, the vectors and the agent are delivered locally. In other embodiments, the vectors and the agents are delivered systemically.

Cell Compositions

In another preferred embodiment, the conditionally silenced vectors expressing pro-angiogenic factors are administered to cells such as myoblasts, myocytes, satellite myoblasts, muscle stem cells, cardiac stem cells, mesenchymal stem cells, hematopoietic stem cells, endothelial progenitor stem cells, fibroblasts, smooth muscle cells, stem cells (bone marrow, peripheral blood, adipocyte, multiple tissue). The cells can be harvested from a patient or donor, purified and cultured ex-vivo. Once expanded, the cells can be transfected, infected or mixed with the conditionally silenced vectors [as viral vectors or plasmid DNA] expressing pro-angiogenic and/or other factors (e.g. stromal derived factor) and administered to a patient. For example, if the patient has presented with myocardial ischemia, the cells are administered to the patient via, for example, intra-cardiac injection. The ischemic injury is thus provided with cells that will integrate and/or differentiate into cardiac cells, vessels etc, and the pro-angiogenic growth factors induce or promote the vascularization of the injured tissue.

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

As used herein, the phrases "subpopulation of bone marrow-derived adherent stem cells", "Sca-1$^+$/CD45$^-$/ckit$^-$/CD90$^+$/CD105$^-$ Stem cells", "CD34$^+$/CD45$^-$/ckit$^-$/CD90$^+$/CD105$^-$ Stem cells", "Sca-1$^+$/CD45$^-$/ckit$^-$/CD90$^+$/CD105$^-$ cells (BMMSC)", "Sca-1$^+$/CD45$^-$/c-kit$^-$/Thy1$^+$/CD105$^-$, and mesenchymal stem cell subpopulation" are used interchangeably and refer to a subpopulation of bone marrow cells that are isolated from a mixed population of bone marrow-derived adherent stem cells by the methods disclosed herein. In some embodiments, the subpopulation of bone marrow-derived adherent stem cells is isolated by isolating from a mixed population of bone marrow-derived adherent stem cells a subpopulation of said cells that are Sca-1$^+$ or CD34$^+$ as well as CD45$^-$/c-kit$^-$/Thy1$^+$/CD105$^-$, depending on the source of the bone marrow-derived adherent stem cells. For example, if the source of the bone marrow-derived adherent stem cells is a mouse, the subpopulation of said cells can include those cells that are Sac-1$^+$/CD45$^-$/c-kit$^-$/Thy1$^+$/CD105$^-$. If the source of the bone marrow-derived adherent stem cells is a human, the subpopulation of said cells can include those cells that are CD34$^+$/CD45$^-$/c-kit$^-$/Thy1$^+$/CD105$^-$.

The isolation of the disclosed subpopulations can be performed using any methodology including adherence to plastic culture dishes followed by culture in a selective medium or and/of methodologies that can separate cells based on expression or lack of expression of the one or more of the CD133, CD45, CD34, CD31, Sca-1, c-kit, Thy1, and CD105 markers including, but not limited to fluorescence-activated cell sorting (FACS).

The stem cells used in accordance with the invention are, in order of preference, autologous, allogeneic or xenogeneic, and the choice can largely depend on the urgency of the need for treatment. A patient presenting an imminently life threatening condition may be maintained on a heart/lung machine while sufficient numbers of autologous stem cells are cultured or initial treatment can be provided using other than autologous stem cells.

The cell therapy of the invention can be provided by several routes of administration, including the following. First, intracardiac muscle injection, which avoids the need for an open surgical procedure, can be used where the stem cells are in an injectable liquid suspension preparation or where they are in a biocompatible medium which is injectable in liquid form and becomes semi-solid at the site of damaged myocardium. A conventional intracardiac syringe or a controllable arthroscopic delivery device can be used so long as the needle lumen or bore is of sufficient diameter (e.g. 30 gauge or larger) that shear forces will not damage the stem cells. The injectable liquid suspension stem cell preparations can also be administered intravenously, either by continuous drip or as a bolus. During, open surgical procedures, involving direct physical access to the heart, all of the described forms of stem cell delivery preparations are available options.

As a representative example of a dose range is a volume of about 20 to about 50 µl of injectable suspension containing about $10-40 \times 10^6$ cells/ml. The concentration of cells per unit volume, whether the carrier medium is liquid or solid remains within substantially the same range. The amount of stem cells delivered will usually be greater when a solid, "patch" type application is made during an open procedure, but follow-up therapy by injection will be as described above. The frequency and duration of therapy will, however, vary depending on the degree (percentage) of tissue involvement, as already described (e.g. 5-40% left ventricular mass).

In cases having in the 5-10% range of tissue involvement, it is possible to treat with as little as a single administration of one million cells in 20-50 µl of injection preparation. The injection medium can be any pharmaceutically acceptable isotonic liquid. Examples include phosphate buffered saline (PBS), culture media such as DMEM (preferably serum-free), physiological saline or 5% dextrose in water.

In cases having more in a range around the 20% tissue involvement severity level, multiple injections of 20-50 µl ($10-40 \times 10^6$ cells/ml) are envisioned. Follow-up therapy may involve additional dosings.

In very severe cases, e.g. in a range around the 40% tissue involvement severity level, multiple equivalent doses for a more extended duration with long term (up to several months) maintenance dose aftercare may well be indicated.

In another embodiment, the isolated and culture expanded cells can be utilized for the implantation of various prosthetic devices. For example, using porous ceramic structures filled with culture-expanded human cells, and implanting these structures in areas where there is extensive tissue damage.

In other embodiments, different stem cells can be used with the mesenchymal stem cells in the treatment of heart and peripheral diseases and disorders thereof. Preferably, the stem cells are totipotent or pluripotent stem cells.

There are many undifferentiated cells found in vivo. Stem cells are undifferentiated immature cells, capable of self renewal (division without limit) and differentiation (specialization). These juvenile cells are abundant in a developing embryo, however, their numbers decrease as development progresses. By contrast, an adult organism contain limited number of stem cells which are confined to certain body compartments.

It is generally believed that stem cells are either monopotent, bipotent or pluripotent. Monopotent and bipotent stem cells are more restricted in development and give rise to one or two types of specialized cells, respectively. In contrast, the pluripotent stem cells (PSCs) can differentiate into many different types of cells, giving rise to tissue (which constitute organs) or in the case of totipotent stem cells, the whole organism. Pluripotent stem cells, unlike monopotent or bipotent, are capable of multilineage differentiation, giving rise to a tissue which would consist of a collection of cells of different types or lineages.

According to the current understanding, a stem cell, such as a pluripotent stem cell, has the following four characteristics: (i) it is an undifferentiated cell—i.e. it is not terminally differentiated; (ii) it has the ability to divide without limit; (iii) it has the ability to give rise to differentiated progeny; and (iv) when it divides each daughter has a choice: it can either remain as stem cell like its parent or it can embark on a course leading to differentiation.

The hematopoietic stem cell is an example of a pluripotent stem cell which is found among marrow cells and gives rise to all the various blood cells (including leucocytes and erythrocytes). Hemopoietic stem cells can be extracted by isolation from (i) bone marrow, (ii) growth factor mobilized peripheral blood or (iii) cord blood (placenta). Recently, hemopoietic stem cells have been prepared from Embryonic Stem cells (ES), which are extracted from embryos obtained using in vitro fertilization techniques. These undifferentiated cells are capable of multi-lineage differentiation and reconstitution of all body tissue i.e. are totipotent.

There are a number of undifferentiated stem cells of the hemopoietic lineage. These include pluripotent stem cells (PSCs), lymphoid stem cells (LSCs) and myeloid stem cells known collectively as lymphohaematopoietic progenitor cells (LPCs). LSCs and myeloid stem cells are each formed by the differentiation of PSCs. Hence, LSCs and myeloid stem cells are more committed than PSCs. Examples of differentiated cells of the hemopoietic lineage include T cells, B cells, eosinophils, basophils, neutrophils, megakaryocytes, monocytes, granulocytes, mast cells, and lymphocytes.

Other stem cells include neural stem cells, multipotent stem cells that can generate neurons, atrocytes and oligodendrocytes (Nakafuku and Nakamura, 1995, *J. Neurosci Res.*, vol 41(2): 153-68; Anderson, 1994, *FASEB J.*, vol 8(10): 707-13; Morshead et al., 1994, *Neuron*, Vol 13(5): 1071-82). Skeletal muscle satellite cells are another type of stem cell, more specifically a distinct class of myogenic cells that are maintained as quiescent stem cells in the adult and can give rise to new muscle cells when needed (Bischoff, 1986, *Dev Biol.*, vol 115(1): 129-39). Other types of stem cells are epithelial stem cells, a subset of basal cells, and mesenchymal stem cells.

Embryonic stem (ES) cells are routinely used in the production of transgenic animals. ES cells have been shown to differentiate in vitro into several cell types including lymphoid precursors (Potocnik et al., 1994, *EMBO J.*, vol 13(22): 5274-83) and neural cells. ES cells are characterized by a number of stage-specific markers such as stage-specific embryonic markers 3 and 4 (SSEA-3 and SSEA-4), high molecular weight glycoproteins TRA-1-60 and TRA-1-81 and alkaline phosphatase (Andrews et al., 1984, *Hybridoma*, vol 3: 347-361; Kannagi et al., 1983, *EMBO J.*, vol 2: 2355-2361; Fox et al., 1984, *Dev. Biol.*, vol 103: 263-266; Ozawa et al., 1985, *Cell. Differ.*, vol 16: 169-173).

Various antigens are associated with undifferentiated and differentiated cells. The term "associated" here means the cells expressing or capable of expressing, or presenting or capable of being induced to present, or comprising, the respective antigen(s). Most undifferentiated cells and differentiated cells comprise Major Histocompatibility Complex (MHC) Class I antigens and/or Class II antigens. If these antigens are associated with those cells then they are called Class I$^+$ and/or Class II$^+$ cells. Each specific antigen associated with an undifferentiated cell or a differentiated cell can act as a marker. Hence, different types of cells can be distinguished from each other on the basis of their associated particular antigen(s) or on the basis of a particular combination of associated antigens. Examples of these marker antigens include the antigens CD34, CD19 and CD3. If these antigens are present then these particular cells are called CD34$^+$, CD19$^+$ and CD3$^+$ cells respectively. If these antigens are not present then these cells are called CD34$^-$, CD19$^-$ and CD3$^-$ cells respectively.

Some of the markers identified on myeloid stem cells comprise $CD34^+$ $DR^+$, $CD13^+$, $CD33^+$, $CD7^+$ and $TdT^+$ cells. PSCs are $CD34^+$ $DR^-$ $TdT^-$ cells (other useful markers being $CD38^-$ and $CD36^+$). LSCs are $DR^+$, $CD34^+$ and $TdT^+$ cells (also $CD38^+$). Embryonic stem cells express SSEA-3 and SSEA-4, high molecular weight glycoproteins TRA-1-60 and TRA-1-81 and alkaline phosphatase. They also do not express SSEA-1, the presence of which is an indicator of differentiation. Other markers are known for other types of stem cells, such as Nestein for neuroepithelial stem cells (*J. Neurosci*, 1985, Vol 5: 3310). Mesenchymal stem cells are also positive for SH2, SH3, CD29, CD44, CD71, CD90, CD106, CD120a and CD124, for example, and negative for CD34, CD45 and CD14.

Stem cells may further be isolated for transduction and differentiation using known methods. For example, in mice, bone marrow cells are isolated by sacrificing the mouse and cutting the leg bones with a pair of scissors. Stem cells may also be isolated from bone marrow cells by panning the bone marrow cells with antibodies which bind unwanted cells, such as $CD4^+$ and CD8+ (T cells), $CD45^+$ (panB cells), GR-1 (granulocytes), and Iad (differentiated antigen presenting cells). For an example of this protocol see, Inaba et al., *J. Exp. Med.* 176:1693-1702 (1992).

In humans, $CD34^+$ hematopoietic stem cells can be obtained from a variety of sources including cord blood, bone marrow, and mobilized peripheral blood. Purification of $CD34^+$ cells can be accomplished by antibody affinity procedures. An affinity column isolation procedure for isolating $CD34^+$ cells is described by Ho et al., *Stem Cells* 13 (suppl. 3): 100-105 (1995). See also, Brenner, *Journal of Hematotherapy* 2: 7-17 (1993). Methods for isolating, purifying and culturally expanding mesenchymal stem cells are known.

Alternatively, or in addition, many cells can be identified by morphological characteristics. The identification of cells using microscopy, optionally with staining techniques is an extremely well developed branch of science termed histology and the relevant skills are widely possessed in the art.

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells will be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

The isolating step can be performed in a stepwise manner and/or concurrently. For example, the presence or absence of each marker can be assessed individually, producing two subpopulations at each step based on whether the individual marker is present. Thereafter, the subpopulation of interest can be selected and further divided based on the presence or absence of the next marker.

It is also understood that different separation techniques (e.g., affinity purification and FACS) can be employed together at one or more steps of the purification process.

Administration

Suitable methods for administration of the compositions of the invention, such as, for example, conditionally silenced vectors, cells comprising the vectors, etc, include, but are not limited to intravenous administration and delivery directly to the target tissue or organ. In some embodiments, the method of administration encompasses features for regionalized delivery or accumulation of the compositions at the site in need of treatment. In some embodiments, the compositions are delivered directly into the tissue or organ to be treated. In some embodiments, selective delivery of, for example, the cells, is accomplished by intravenous injection of cells, where they home to the target tissue or organ and engraft therein. In some embodiments, the presently disclosed cells home to the target tissue or organ as a result of the production of an SDF-1 gradient produced by the target tissue or organ, which acts as a chemotactic attractant to the cells.

Such methods may be carried out in any animal in need of treatment. Preferably, the animal is a mammal, more preferably a primate and more preferably still, a human. Thus, although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Dose: An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

In addition to the utilities discussed above, compositions (e.g., expression vectors containing chimeric genes of the present invention) and methods of the present invention also have a number of applications in animal medicine. Although animals do not usually develop classical atherosclerosis, cardiomyopathies are very common. A number of species develop ischemia-related syndromes, including arteritis, vasculitis, and related vasculopathies, that result in direct redox damage to cells and tissues, particularly to vascular walls and myocardial tissues. Such conditions may be alleviated by administration of chimeric genes of the present invention.

A common and serious condition in horses and ponies involves ascending colonic ischemia, usually caused by strangulation obstruction. A related disease in dogs is called gastric dilation-volvulus. Treatment of these disorders typically involves surgical removal of the obstruction. Reperfusion following such surgery can result in significant injury to reperfused tissues, and typically triggers an inflammatory response with progressive tissue necrosis. The reperfusion may also results in death of the animal due to cardiogenic shock. Compositions and methods of the present invention may be used therapeutically to treat such conditions, and to provide protection to vulnerable tissues, including heart and vascular endothelium, during the treatment of the above syndromes.

Another utility of the present invention is the treatment of cardiac disease in cats and dogs. A variety of forms of cardiovascular disease have been described in both cats and dogs, including dilated cardiomyopathy, left ventricular hypertrophy, and hyperthyroidism. Systemic necrotizing vasculitis, a condition that may be analogous to atherosclerosis in humans (with regard to plaque formation and intimal proliferation), has been described in Beagles. Each of these conditions may involve ischemia and reperfusion redox injuries to cardiac and vascular tissue that may be treated using the methods and compositions of the present invention.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Therapeutic Vasculogenesis Angiogenesis and Arteriogenesis of Ischemic Skeletal Muscle by a Conditionally Silenced AAV9 Gene Therapy Vector Expressing Human VEGF Hypothesis: VEGF gene delivery in a semi-permanent, muscle-tropic AAV9 vector driven by a hypoxia-regulated promoter will support directional angiogenesis followed by arteriogenesis and re-establishment of a functional vascular network with stable tissue reperfusion.

Materials and Methods: The human (h)VEGF gene driven by a PGK promoter containing tandem arrays of HIF-1a and NSF (silencer) binding sites was cloned into an AAV9 vector. Gene expression and regulation were quantified in hypoxic skeletal myocytes and ischemic hind limbs of normal and atherosclerosis-prone mice. Arteriogenic and angiogenic therapy were evaluated in a mouse hind limb ischemia model using intramuscular delivery of the AAV9-CS-VEGF vector.

Results: The results shown here indicate for the first time that sustained VEGF delivery by a hypoxia-regulated vector promotes stable reperfusion of ischemic tissue.

The methods involve the transfer of the VEGF gene using an adeno-associated viral (AAV) vector wherein VEGF expression is regulated by a phosphoglycerate kinase (PGK) promoter with a combined cassette of hypoxia response elements (HREs) and silencer elements that confers silencing of gene expression under aerobic conditions and activation of expression by ischemia. The vector is named AAV9-CS-VEGF. A control AAV9 vector expressing VEGF directed by the PGK promoter without the silencer regulatory elements was also created; the control is named AAV9-PGK-VEGF. By using the protocol it was demonstrated that angiogenesis was followed by arteriogenesis with the generation of stable blood vessels and reperfused tissue only when using AAV9-CS-VEGF treatment.

The AAV9-CS-VEGF and AAV9-PGK-VEGF vectors were created and tested for stable vessel production and transgene regulation by ischemia. Hindlimb ischemia was implemented in Balb/C mice by ligation and excision of the femoral artery. Limbs were injected with $10^{10}$ pfu of AAV9-CS-VEGF or AAV9-PGK-VEGF, and controls were injected with VEGF expressed by an adenoviral vector or phosphate buffered saline. Limbs were scanned bi-weekly for blood perfusion by the laser Doppler technique and vessels were imaged after sacrifice using DiI fluorescence and confocal microscopy or fluorescent antibody stains. The results show, for the first time, that AAV9-CS-VEGF induced angiogenesis over the first 2-4 weeks followed by arteriogenesis with the production of vessels of similar size to the original excised femoral artery after 16 weeks of continuous VEGF production, AAV9-CS-VEGF also produced vessels that grew longitudinally from hip to foot, a result not seen with adenovirus or AAV9-PGK-VEGF despite hypoxia-regulation of the latter vector. The ability of the new of vessels to grow in a longitudinal manner may be due to the directional cues provided by graded hypoxia regulation combined with silencing in normoxic regions of the muscle. This feature may be responsible for the transition to arteriogenesis caused by the shear stress of directional blood flow. It was also shown that arteries can be produced using a AAV2-CS-VEGF construct, transferred into mesenchymal stem cells and injected into rabbit ischemic hind limbs.

Use of vectors AAV9-CS-VEGF or AAV2-CS-VEGF and other pro-angiogenic growth factors for the treatment of muscle ischemia include peripheral and myocardial ischemia.

Summary: Sustained, ischemia-regulated VEGF expression supports early angiogenesis that evolves into arteriogenesis with the generation of stable vessels, muscle perfusion and limb salvage. Down-regulation of the transgene coincident with therapy provides a safety switch that will allow the clinical translation of this strategy to treat patients with critical limb ischemia.

Example 2

Models of Therapeutic Angiogenesis

Figure 1A:
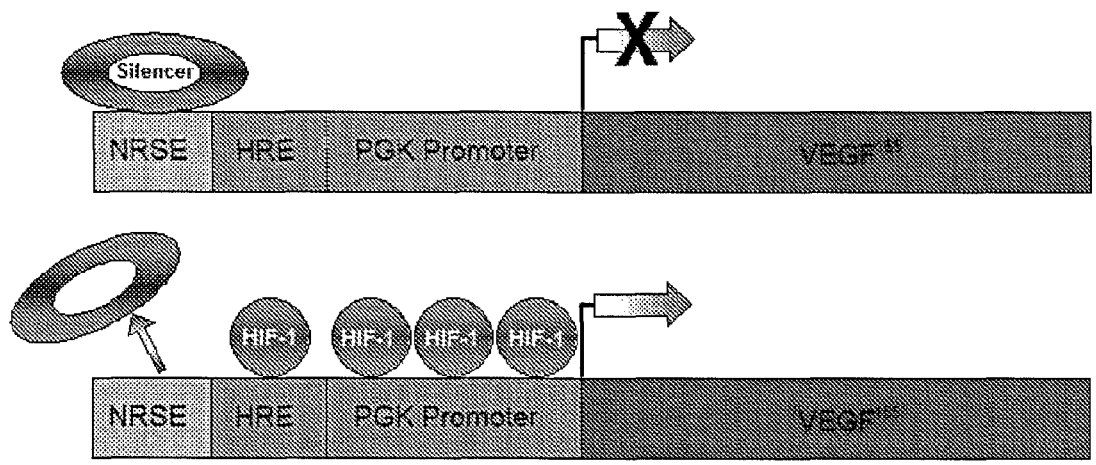
FIGS. 1A-1E: Hypoxia regulated transgene expression.
Figures 1B, 1C, 1D, 1E:
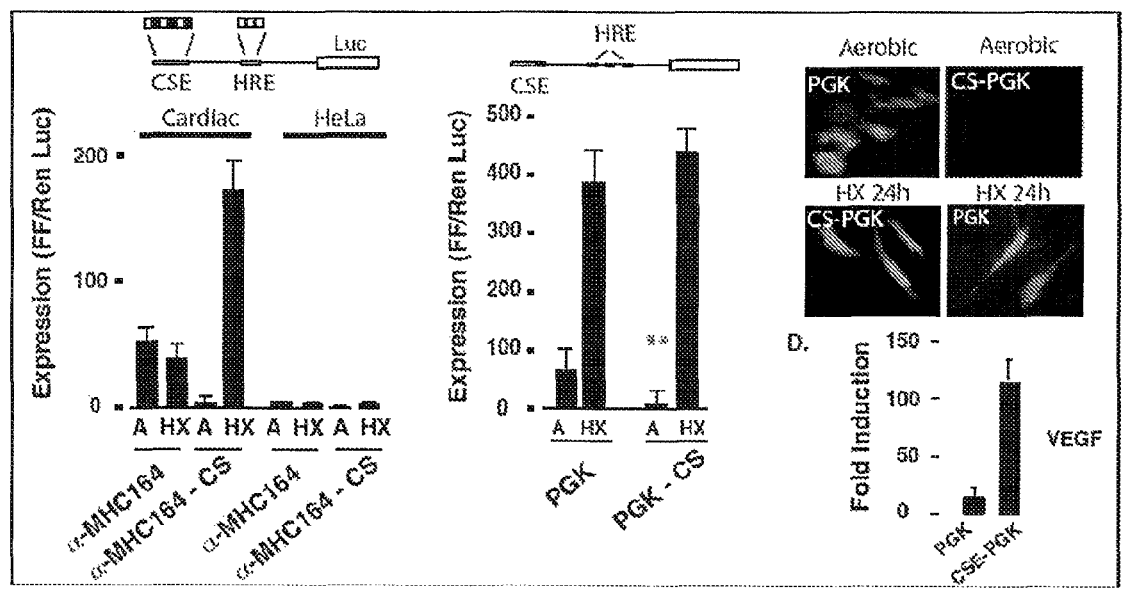
Figures 2A, 2B:
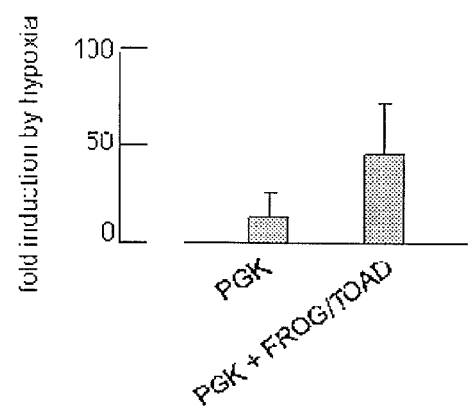
FIG. 2A is a schematic illustration showing the sequences of FROG, TOAD, and FROG+TOAD elements are indicated in FIG. 2C. IRE means inflammatory response element (NFκ-B). Other components of the construct are the same as the NRSE construct described in FIGS. 1A-1E.
FIG. 2B: C2C12 cells were transfected with a plasmid expressing luciferase directed by the PGK promoter containing FROG/TOAD elements+HRE. Cells were exposed to aerobic or hypoxic incubations for 48 h as described in FIGS. 1A-1E.

Expression Profiles of Conditionally Silenced Gene Therapy Vectors: Conditional silencing is a new technique developed in this laboratory to provide more stringent regulation of genes by ischemia. To do this HIF-1a binding elements (HRE) were combined with silencer elements (neuronal response silencer elements (NRSE) and non-tissue specific silencers from the murine Igβ promoter) in tandem arrays upstream of tissue-specific and constitutive promoters. The elements were arranged such that under physiological oxygen tension (normoxia), the silencer elements were active and suppress gene expression. Under hypoxia (or ischemia), HRE sites are activated causing a dual induction of the HIF-1 enhancer and suppression of the silencer elements. The net effect is very low normoxic gene expression that is strongly (>100-fold) induced by hypoxia. The high inducibility is due mostly to the silencing of basal gene expression and does not constitute a hyperactive promoter. FIGS. 1A, 1B and 1C describe conditional silencing of a tissue specific promoter and a strong constitutive promoter with transcriptional activation by hypoxia. The cardiac-specific α-myosin heavy chain (α-MHC) promoter is not hypoxia-inducible. Insertion of 3×HRE elements at −86 bp and a conditional silencing switch element (CSE) containing tandem HREs and silencer elements at −164 as indicated reversibly silences expression and confers 142±36-fold induction by hypoxia in cardiac myocytes. The α-MHC promoter does not express significantly in non-cardiac cells. The phosphoglycerate kinase (PGK) gene promoter has endogenous HREs situated between −280 and −365 upstream of the transcription start site and expression is induced 7.1±0.3-fold in skeletal myocytes by hypoxia. Insertion of a CSE at position −495 resulted in >90% silencing of aerobic expression that was reversed by hypoxia. The fold induction of the CS-PGK promoter was 116±26. FIG. 1D shows examples of CS-PGK-GFP expression after gene delivery to C2C12 skeletal myocytes and subjection to hypoxia. The mechanism of conditional silencing involves antagonism between HDAC activity of silencer binding proteins and HAT activity of the inducible enhancers, and allosteric interference of factors binding to proximal DNA elements. Both of these activities were confirmed by gel mobility shift assays, over-expression of silencer proteins and dominant negative silencer expression, and inhibition of HDAC with trichostatin A.

Without wishing to be bound by theory, aging and disease may reduce HIF-1 activity. A second series of CS-hypoxia response promoters were created in which the HIF-1 binding element was replaced by a hypoxia-responsive metal response element (MRE) from the metallothionein (MT2) gene promoter; consensus TGCRCNC (where R stands for A or G and N for any of the four bases). When combined with silencer elements these promoters retained the same regulation as the HIF-1 cassettes.

Regulation by Ischemia In Vivo: The PGK-VEGF and CS-PGK-VEGF constructs were cloned into AAV9 for in vivo expression and anti-ischemia therapy. AAV9 has tropism for skeletal and cardiac muscle when delivered systemically. AAV9 vectors were delivered by inter-ocular injection of 1-day old mice and by tail vein injections of 8-week mice. FIG. 5A shows 1-day old mice injected with AAV9 with a trypan blue dye tracer to confirm successful delivery. FIG. 5B shows VEGF expression in tissues 4 weeks after injection, PGK-VEGF delivered by AAV9 is preferentially expressed in skeletal cardiac muscles. FIG. 5C shows expression of the conditionally silenced CS-PGK-VEGF construct in the hind limb ankle muscle of 4-week old mice 1-week after femoral artery excision compared with the non-ischemic contralateral limb. Induction of expression by ischemia was 78±6-fold (n=3). In FIG. 5D, a rat fat pad model was used to test for the induction of angiogenesis by unregulated and CS-AAV9-VEGF vectors in non-ischemic tissue. The middle panel shows positive vessel grown when the tissue was injected with unregulated PGK vector compared with no vessels in response to conditionally silenced vector. These results confirm that gene expression from the CS construct is silenced in non-ischemic tissue.

Figures 3A, 3B, 3C:
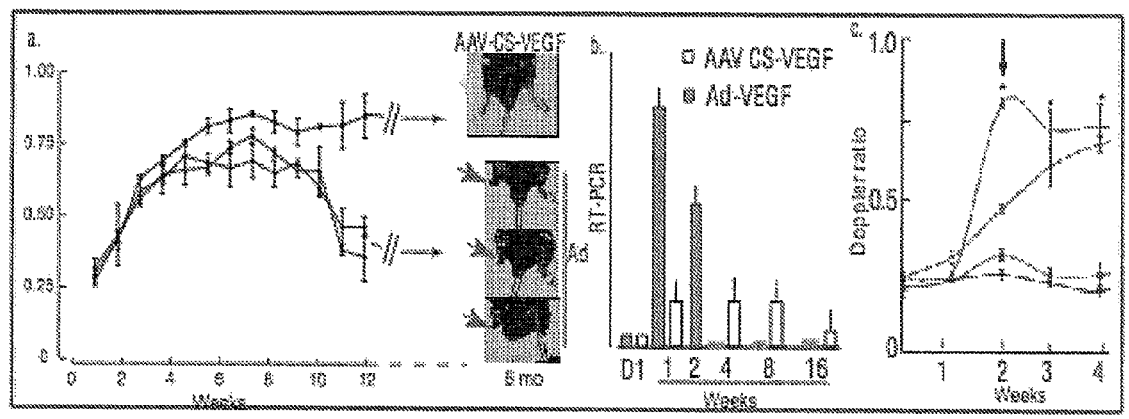
FIGS. 3A-3C show reperfusion of ischemic hind limb by CS-AAV vs. adenovirus.
Figure 4:
FIG. 4 shows an immunostain of paraffin embedded tissue sections using a smooth muscle actin antibody revealing significantly larger vessels in hindlimbs treated with AAV9-CS-VEGF compared with an AAV9-PGK-VEGF vector after 12 weeks (AAV9-PGK-VEGF is regulated by hypoxia through endogenous HREs but without conditional silencing the regulation is lower.
Figure 4:
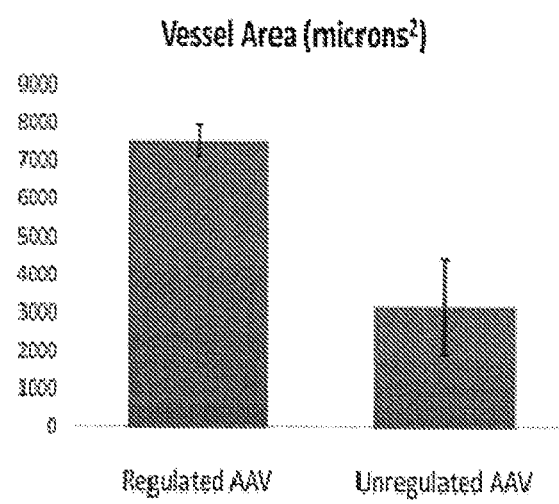

Mouse Hind Limb Model of Arteriogenesis: Therapeutic angiogenesis was quantified in response to AAV9 and adenoviral vectors in a mouse ischemic hind limb model. In the first set of experiments the effects of AAV9-CS-PGK-VEGF delivery were compared with that of low and high dose Ad-CMV-VEGF. These results are shown in FIG. 3A. All treatments improved Doppler scores up to 8-10-weeks but after this there was a precipitous decline of flow in both adenovirus treatment groups while flow in the AAV-CS-VEGF group was sustained over 6-months. As indicated in the right panels, AAV therapy with CS-VEGF resulted in limb salvage whereas all limbs (6 of 6) treated with adenovirus auto-amputated within 6-months. These results show that adenoviral delivery of VEGF does not support sustained generation of blood vessels in the rabbit hindlimb model. In contrast, sustained vessels were generated by AAV-CS-VEGF. FIG. 3B shows VEGF expression determined by real time PCR (RT-PCR); expression by adenovirus was strong during the first week and then declined close to baseline within 8 weeks. VEGF expression driven by CS-AAV9 was sustained as still above baseline at 16 weeks. In FIG. 3C hind limb reperfusion by CS-VEGF was compared with unregulated (PGK)-VEGF. The arrow indicates a time point 2 weeks after gene delivery where the Doppler scores of limbs treated with CS-VEGF are significantly higher than those treated with AAV9-PGK-VEGF. These results evidence that a more regulated expression of VEGF generates more rapid reperfusion despite a lower expression of VEGF mediated by the CS vector. Organized angiogenesis requires a balance between VEGF-mediated endothelial activation Notch-mediated lateral inhibition of endothelial sprouting. VEGF expression was compared with that of a Notch Dll4 target HEY2. These results are shown in FIG. 6 comparing angiogenesis driven by AAV9-PGK-VEGF and AAV9-CS-PGK-VEGF. The results show that the VEGF:HEY2 levels are more balanced when VEGF is regulated by hypoxia and conditional silencing. Note that expression of VEGF in hind limbs containing the CS vector is >6-fold less than that in muscles expressing the unsilenced vector. In the experiments described in FIGS. 3A-3C and 6, reperfusion of the tissue is better supported by lower VEGF expression. It was also found that a peak of SDF-1 expression (3.1-fold) at 14-28 days only in limbs treated with CS-AAV-VEGF.

Directional Vessel Growth by CS-AAV-VEGF: Vessels were imaged by DiI staining of tissue sections every 2 weeks for 10-16 weeks after treatments. FIG. 7A shows examples of vessels in muscle after 12 weeks following VEGF delivery by adenovirus or AAV-CS-VEGF and after 16-weeks of AAV9-CS-VEGF. The bottom panel shows the femoral vein and artery before dissection. Vessels in the Ad-treated sections were oriented diagonally with respect to the direction of the femoral artery whereas larger vessels (arterioles and arteries) in the CS-VEGF treated muscles were oriented in the same, hip to knee direction as the femoral artery and vein. At 16 weeks of treatment with AAV9-CS-VEGF, vessels of similar size to the femoral artery were visualized between the position of the sutures that depict the start of the femoral artery dissection area, indicated by arrows. FIG. 7B shows an arteriole stained with smooth muscle actin (red) and dappi (blue). Vessel areas were quantified in sections of hind limb from AAV9-CS-VEGFAAV9-PGK-VEGF treatments at 16 weeks using NIH image software; data represents at least 50 vessels per condition. Vessels in the AAV9-CS-VEGF treatment group were significantly larger than those in the AAV9-PGK-VEGF group (p<0.02). Capillary density was quantified by staining sections for CD31 and VWF, and using Volocity software, illustrated in FIG. 7C. In this procedure, Z-stacks were obtained by dual photon confocal microscopy with 10 μm steps over a total vertical distance of approximately 200 μm. Twenty image stacks are acquired in 6-minute time intervals. The Z-stacks were then rendered in 3D using Volocity visualization. Each image was individually analyzed for total vessel network volume within the region of interest (ROI). ROI's equal to 90% of the total field were used to evaluate total blood vessel network volume. By this method, vessel density was 1.6-fold higher in the CS-AAV-VEGF treatments at 16 weeks compared with the PGK-AAV-VEGF groups (p<0.05). These results were supported by CD31 and VWF staining of paraffin sections.

Mouse AMI Model: To determine whether VEGF expressed by AAV9 vectors affected ischemia-reperfusion injury and post-infarct remodeling, AAV9-VEGF vectors were delivered systemically as described in FIGS. 5A-5D and AMI implemented after 10-weeks. Infarct size was determined 24 h after reperfusion. Contractility was determined before AMI and 2 weeks post AMI by echocardiography and MRI. These results are shown in Table 1.

TABLE 1

Myocardial contractile parameters calculated from Echo (n = 3).

| Treatment | IVSd mm$^3$ | IVSs mm$^3$ | LVIDd mm$^3$ | LVIDs mm$^3$ | EF % | FS | HR. |
|---|---|---|---|---|---|---|---|
| WT No Ischemia | 0.62 | 1.12 | 3.38 | 2.01 | 85 | 52 | 409 |
| Ischemia 20 min | 0.37 | 0.66 | 4.13 | 3.23 | 44 | 29 | 410 |
| AAV-PGK-VEGF No Ischemia | 0.65 | 1.03 | 3.9 | 2.26 | 77 | 45 | 403 |
| AAV PGK-VEGF 20 min Ischemia | 0.39 | 0.78 | 4.2 | 3.12 | 48 | 26 | 399 |
| AAV-CS-VEGF No Ischemia | 0.67 | 1.1 | 3.95 | 2.18 | 80 | 46 | 401 |
| AAV-CS-VEGF 20 min Ischemia | 0.45 | 0.88 | 4.16 | 2.93 | 69 | 39 | 410 |

Infarct sizes determined by Evans blue and TTC staining (WT: 41%; AAV9-PGK-VEGF: 43%; AAV9-CS-VEGF, 39%; n=3 per group) were no different between vector transformed and untreated (WT) mice. Cardiac contractile parameters and chamber volumes (Table 1) before AMI were not different between vectors or between WT (untreated) mice. After 2-weeks, ejection fraction (EF) and fractional shortening (FS) of non-transduced (WT) mice and mice with AAV-PGK-VEGF displayed similar declines (Table 1; WT: EF 85 to 44, FS 52 to 29; AAV9-PGK-VEGF: EF 77 to 48, FS 45 to 26). However the hearts of mice transformed with AAV9-CS-VEGF displayed improved post-ischemia contractility, with the mean EF declining from 80 to 69 and FS from 46 to 39. MRI confirmed these results. ED volumes were similar but the ES volume of AAV9-CS-VEGF transduced hearts were smaller reflecting larger contractions.

Summary: These results provide evidence that delivery of VEGF using a hypoxia-regulated conditionally silenced AAV9 vector improved muscle performance after ischemia in both ischemic hind limb and AMI models. VEGF expression by AAV9-CS-VEGF in the hind limb was 10-fold less than the equivalent expression from the non-silenced vector. This indicates that low expression confined strictly to regions of hypoxia is preferable to higher unregulated expression. It may be that at least one reason for this is a more balanced ratio of VEGF:Notch signaling in the former condition. Results from the hind limb model also evidence that CS-regulated VEGF confers directionality to vessel growth that was not seen with constitutive expression by adenovirus or AAV and that the degree of therapy is determined by the level of conditional silencing with the greatest effect seen when all 3 silencer elements including NRSE, FROG, TOAS are present. These results show that hypoxia dictated directional vessel growth in their soft tissue ischemia model by creating gradients of growth factors (VEGF, SDF-1) that provide cues for EPC homing and presumably endothelial cell sprouting down the gradient. It was also found that large arteries formed in the muscles of AAV-CS-VEGF treatment groups 16 weeks after gene delivery. Without wishing to be bound by theory, it is proposed that this is a secondary response to directional vessel growth and involves shear stress generated as vessel networks make connections upstream and downstream of the region of the excised femoral artery and blood flow resumes from hip to ankle.

Example 3

Age-Related Decline of Multiple Pro-Angiogenic Growth Factors, Depressed Induction of Hypoxia-Regulated Genes, and Depressed Migration of EPC Age-Mediated Decline of Angiogenic Growth Factor Gene Expression in Murine BM-MSC: MSCs were isolated from the tibias and femurs of 2-month and 26-month old mice by attachment and culture in MesenCult Media with MSC supplements (Stem Cell Technologies), 4 mice per age group. Cells were treated identically and passaged to reach homogeneity, determined by FACS analysis of cell surface markers Sca-1, CD44, CD45, and CD11b. All cells were equivalently competent to differentiate into chondrocytes, osteocytes and adipocytes when subject to the appropriate inducers. RNA was purified at passage 11 under identical culture conditions and transcripts analyzed by microarray. RT-PCR confirmed changes in selected growth factor-associated gene transcripts. There were significant decreases of angiopoietin 2 (3-fold), Hgf (272-fold) Igf-1 (26-fold), VEGFa (4.2-fold), VEGFc (3-fold) and the p85 subunit of PI3-kinase Pi3r1 (3.5-fold). Transcript levels of the VEGF receptor Flt1 increased. Secreted levels of VEGF and SDF-1 from 2-mo and 26-mo MSC was measured during hypoxic culture by ELISA and Western blot respectively. Hypoxia increased VEGF and SDF-1 after 48 h by 8- and 9.5-fold respectively only from 2-month cells whereas there was no significant induction of either from 26-month cells. Similar results were found for Sonic Hedgehog. To confirm these results and assign biological significance, spent media from 48 h hypoxic cells was used in HUVEC Matrigel tube assays and for injection into ischemic mouse hind limbs. In both assays media from 2-month but not 26-month cells supported angiogenesis indicated by tube formation in the Matrigel assay and limb salvage and increased Doppler score in the hind limb.

Summary: These studies on mouse MSC revealed significant age-related declines in the expression of multiple growth factors, in particular HGF, VEGF and IGF-1 and a muted response to hypoxia that resulted in suppressed induction of VEGF, SDF-1 and Shh. The biological consequence of this is evident from the absence of angiogenesis in 2 models by conditioned medium from aged MSCs. These results support that VEGF is decreased in animal and human EPCs by aging and is consistent with a reduced therapeutic benefit of autologous MSCs or EPCs in aged subjects. These studies also evidence that age decreases the mobility and activation of $CXCR4^+$ cells in the bone marrow, and reduce the migration of these towards SDF-1, effects that correlate with suppressed homing and revascularization.

Example 4

Soft Dermal tissue Ischemia Model

This model consists of lateral skin incisions (2.5 cm in length and 1.25 cm apart) created on the dorsal surface of mice, penetrating the skin, dermis, and underlying adipose tissue. The overlying skin is undermined, and a 0.13-mm-thick silicone sheet (Invotec International, Jacksonville, Fla.) is inserted to separate the skin from the underlying tissue bed. The skin is then reapproximated with 6-0 nylon sutures. The existing vessels in the tissue are degraded and new vessels develop longitudinally in the direction of the hypoxia gradient that is also longitudinal because the tissue remains connected to the circulation at either end of the silicone sheet. This model was reproduced in order to quantify angiogenesis and vasculogenesis in response to gene and stem cell therapy in various diseases. Results indicated an apparent reorientation of vessels during revascularization. In sham surgery lateral incisions were made but the silicone sheet was not inserted. Two hours after surgery there was minimal blood flow at the midline consistent with severance of vessels. These vessels were re-established by day 7 and progressed towards the midline where flow also resumed. In wild type mice with ischemia, residual flow at the right and left edges were similar to the sham at 2 h post surgery but this perfusion was absent at day 7, consistent with vessel degeneration, and replaced by midline flow that most likely originated from the distal and proximal ends. The same surgery on 1-year old $ApoE^{-/-}$ mice fed high fat resulted in poor circulation 2 h post-surgery that was only mildly improved after 7 days. The Doppler ratio of these mice was significantly lower than wild type at both time points evidencing more rapid vessel decay and defective responses of the tissues to ischemia. These defects were likely to involve combinations of reduced ability of the tissue to attract BM stem cells and reduced function of the BM cells. $ApoE^{-/-}$ mice but not wild types displayed areas of necrosis after 7 days. DiI staining indicated a rapid decay of capillaries after implementation of ischemia and generation of new longitudinal vessels. Doppler images of 1-year old $ApoE^{-/-}$ mice at D3 and D10 after left hind limb ischemia showed that limbs that received AAV-GFP showed signs of necrosis at D10 but were salvaged by AAV9-CS-VEGF confirming efficacy of gene therapy in these mice.

Human Cell Studies: To determine whether age and disease effected molecular genetic changes in human bone marrow cells $CD34^+/Lin^-$ cells were isolated from the bone marrow of 5 patients with CAD, 5 age-matched patients undergoing cardiothoracic surgery for non-CAD related conditions, and 2 healthy volunteers. Cells (5-20 mL) were collected by bone marrow aspiration from the sternum during surgery. Mononuclear cells were isolated by Histopaque and the cells frozen in 50% IMDM, 40% FBS and 10% DMSO at a density of $10^7$ cells/ml. CD34+/Lin− cells were purified by affinity binding to magnetic beads and gene expression in purified cells was measured by microarray and rtPCR; VEGF expression was decreased >2-fold in cells from CAD patients. Before analysis, frozen cells were thawed, re-analyzed by FACS. Cell numbers recovered in each group are shown in Table 2.

TABLE 2

|  | Cell# | Lin− | Viability | Lin−/CD34+ | Lin−CD34+ |
|---|---|---|---|---|---|
| Commercial | $1.2 \times 10^8$ | $3.2 \times 10^7$ | $3.8 \times 10^6$ 80% | $0.5 \times 10^5$ | 76% |
| Volunteer | $2.5 \times 10^8$ | $1.5 \times 10^8$ | $2.1 \times 10^6$ 82 | $0.5 \times 10^3$ | 47 |
| Non CAD | $8.7 \times 10^7$ | $5 \times 10^7$ | $2.1 \times 10^6$ 92 | $0.3 \times 10^5$ | 77 |
| CAD | $1.1 \times 10^8$ | $6.3 \times 10^7$ | $5.4 \times 10^7$ 87 | $0.5 \times 10^5$ | 79 |

Similar patterns of $CD34^+/Lin^-$ cells were obtained from each sample by FACS, and the results from Table 3 indicated similar yields of viable $CD34^+/Lin^-$ cells from each sample group relative to the input. VEGF is normally regulated by hypoxia and without wishing to be bound by theory, it was hypothesized that hypoxia-induced VEGF would be decreased in the CAD group similar to an aged mouse MSC. The large decrease of VEGF-A and D in both patient groups was noted as compared with healthy volunteer that may be age-related.

Summary: For the first time dramatic changes of angiogenic genes in $CD34^+/Lin^-$ bone marrow cells of patients with CAD were revealed.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of treating a patient having a disease or disorder associated with hypoxia or ischemia, comprising directly administering to the patient a composition comprising a conditionally silenced vector comprising: at least one FROG element, at least one TOAD element, at least one hypoxia response element (HRE), a gene encoding at least one growth factor, and a promoter upstream of the gene that is in operable linkage with the gene, the at least one FROG element, the at least one TOAD element, and the at least one HRE, in a therapeutically effective controlled amount for inhibiting necrosis and increasing blood flow in ischemic or hypoxic tissue or organ, wherein the growth factor is not expressed in aerobic tissue but is expressed in the ischemic or hypoxic tissue, wherein the at least one FROG element consists of a nucleotide sequence selected from the group consisting of: SEQ ID NOS: 3 and 4, and the at least one TOAD element consists of a nucleotide sequence selected from the group consisting of: SEQ ID NOS: 1 and 2.

2. A method of treating a patient having a disease or disorder associated with hypoxia or ischemia, comprising directly administering to the patient a composition comprising a conditionally silenced vector comprising: at least one FROG element, at least one TOAD element, at least one hypoxia response element (HRE), a gene encoding at least one growth factor, and a promoter upstream of the gene that is in operable linkage with the gene, the at least one FROG element, the at least one TOAD element, and the at least one HRE, in a therapeutically effective controlled amount for inhibiting necrosis and increasing blood flow in ischemic or hypoxic tissue or organ, wherein the growth factor is not expressed in aerobic tissue but is expressed in the ischemic or hypoxic tissue, wherein the at least one FROG element and the at least one TOAD element consist of a nucleotide sequence selected from the group consisting of: SEQ ID NOS: 5 and 6.

3. The method of claim 1, wherein the vector further comprises at least one neuronal responsive silencer element (NRSE).

4. The method of claim 1, wherein the at least one growth factor is selected from the group consisting of: endothelial growth factor, fibroblast growth factor (FGF), platelet derived growth factor (PDGF), insulin-like growth factor (IGF), epidermal growth factor (EGF), transforming growth factor (TGF), hepatocyte growth factor, proliferin, angiotropin, angiopoietin, vascular endothelial growth factor (VEGF), transforming growth factor-beta (TGF- beta), insulin like growth factor-1 (IGF-1), nerve growth factor (NGF), stromal derived factor (SDF), stem cell factor (SCF), and erythropoietin (EPO).

5. The method of claim 1, wherein the tissue or organ is cardiac tissue or limb tissue.

6. The method of claim 1, wherein the composition is administered intramuscularly.

7. The method of claim 5, wherein the tissue or organ is limb tissue and the composition is administered intramuscularly.

8. The method of claim 1, wherein the growth factor is not expressed in normoxic brain cells and normoxic stem cells.

9. The method of claim 1, wherein the conditionally silenced vector comprises a combined cassette of HREs and TOAD and FROG elements.

* * * * *